United States Patent [19]

Junker

[11] Patent Number: 4,668,912
[45] Date of Patent: May 26, 1987

[54] EDDY CURRENT INSPECTION PROBE AND METHOD FOR ASSEMBLING SAME

[75] Inventor: Warren R. Junker, Monroeville Boro, Pa.

[73] Assignee: Westinghouse Electric Corp., Pittsburgh, Pa.

[21] Appl. No.: 698,487

[22] Filed: Feb. 5, 1985

[51] Int. Cl.⁴ .............................................. G01N 27/82
[52] U.S. Cl. ........................................ 324/220; 378/60
[58] Field of Search ...................... 324/220, 221, 219; 104/138 G, 155; 250/358.1; 378/60

[56] References Cited

U.S. PATENT DOCUMENTS 2,622,125 12/1952 Bender ................................ 324/220
4,303,884 12/1981 Malick ................................ 324/220
4,403,551 9/1983 Slight ............................. 104/138 G Primary Examiner—Reinhard J. Eisenzopf
Assistant Examiner—Robert Mueller
Attorney, Agent, or Firm—L. A. DePaul

[57] ABSTRACT

An inflatable eddy current inspection probe having a molded central body embedding therein a plurality of eddy current coils and the leads therefore. The central body is expanded at will by introduction of water or air through a pressure hose connected to the central body to produce effective contact between the coils and the inside wall of a tube.

1 Claim, 4 Drawing Figures

EDDY CURRENT INSPECTION PROBE AND METHOD FOR ASSEMBLING SAME

BACKGROUND OF THE INVENTION

This invention relates to inspection devices and, more particularly, to an inflatable eddy current probe and a method for assembling such a probe which inspects the internal surfaces of a tubular member in, for example, a nuclear steam generator.

DESCRIPTION OF THE PRIOR ART

Eddy current inspection probes have been used extensively for the detection and characterization of discontinuities in thin wall tubing. An application of particular importance is the nuclear industry, wherein the heat transfer tubing used in a nuclear steam generator must be inspected.

More particularly, a typical nuclear steam generator of the type generally referred to herein is more fully described in commonly owned U.S. Pat. No. 4,303,043, issued to MALICK, and is shown in FIG. 1 herein. The nuclear steam generator is referred to generally by reference numeral 20, and comprises a vertical, outer shell 22 with a primary fluid inlet nozzle 24 and a primary fluid outlet nozzle 26 attached near the lower end. A vertical, inner shell 23, also known as a wrapper barrel, has at its lower end a tubesheet 28, having tube holes 30 formed therein. Tubes 38, which are heat transfer tubes shaped with a U-like curvature, are disposed within the wrapper barrel 23, through horizontal tube support plates 33, and are welded to the tubesheet 28 at the tube holes 30. The tubes 38, which may number about 7,000, form collectively what is known as a tube bundle 40. A dividing plate 32, which is attached to both the tubesheet 28 and the outer shell 22, defines a primary fluid, inlet plenum 34 and a primary fluid, outlet plenum 36. Further, a secondary fluid, inlet nozzle 42 is disposed on the outer shell 22, while a steam outlet nozzle 44 is attached to the top of the outer shell 22. Finally, manways 46 are provided through the outer shell 22 to provide access to both the primary fluid, inlet plenum 34 and the primary fluid, outlet plenum 36, so that access may be had to the entire tubesheet 28.

In operation, primary fluid enters the primary fluid, inlet nozzle 24, flows into the primary fluid, inlet plenum 34, ascends the tubes 38, flows around the U-shaped curvatures of the tubes 38, flows into the primary fluid, outlet plenum 36, and exits the steam generator 20 through the primary fluid, outlet nozzle 26. Simultaneously, heat is transferred from the primary fluid to a secondary fluid surrounding the tubes 38, which causes the secondary fluid to vaporize. The resulting steam then exits the steam generator 20 through the steam outlet nozzle 44.

Since the primary fluid contains radioactive particles and is isolated from the secondary fluid by the tubes 38 and the tubesheet 28, it is important that the tubes 38 be maintained defect-free so that no breaks will occur in the tubes 38 or in the welds between the tubes 38 and the tubesheet 28, thus preventing contamination of the secondary fluid by the primary fluid. Of course, since radioactivity exists and because the tubes 38 are small, remote inspection is required.

The following eddy current probes are known for remote inspection of steam generator tubing.

One type of eddy current probe is the "bobbin"-type, wherein two coils of copper wire are wound circumferentially around a relatively rigid core to create the test coil. Although widely and relatively successfully used, the relatively rigid bobbin-type probes are limited to inspecting straight or nearly straight tubes. When it becomes necessary to inspect regions of geometrical transition (expansions, sleeved regions, dents, etc.), bobbin-type probes are generally ineffective.

Another type of eddy current probe is the spring-loaded, "array coil" type of probe. This probe includes individual coils spring or plunger mounted to a relatively rigid central body. This type of probe, however, has a complex structure, is high in manufacturing cost and exhibits poor durability.

Finally, there is known the "inflatable" array coil type of probe, an example of which is also described in commonly owned U.S. Pat. No. 4,303,884, issued to MALICK and which is shown in FIG. 2 herein. FIG. 2 shows a probe 50 comprising generally separate nose 52, rigid central body 54, and tail 56 portions, which are constructed of nylon and are firmly attached together. A bore 58 extends the entire length of the probe 50 and has disposed therein a stainless steel, flexible, "emergency" cable 60 connected to the nose 52. The cable 60 is used to pull the inflated probe 50 out of a particular tube 38, when it becomes caught. Bellows tubing 64 is connected to the tail 56 and acts as a connector between the probe 50 and a long section of stiff nylon tubing 66. The nylon tubing 66 acts as a push rod for remotely inserting the inflated probe 50 through the tubes 38 and carries the electrical leads 97 from the probe 50 to instrumentation located outside the steam generator 20.

A first positioning mechanism 68 is mounted at the nose 52, while a second positioning mechanism 70 is mounted at the tail 56, so as to provide means by which the probe 50 can be centrally oriented within a particular tube 38. Each mechanism 68 and 70 usually includes flexible brushes 72 attached between rubber O-rings 74.

A separate inflation mechanism 76, comprising a thin, cylindrical, rubber tube 78, is disposed over the central body 54. The rubber tube 78 is sealed to the central body 54 at its ends by second O-rings 80.

The central body 54 also has a channel 82 formed therein connected to a vinyl tube 84 in order that a hypodermic syringe may be inserted into the outer end of the vinyl tube 84 for pressurizing of the inflation mechanism 76.

Uniformly spaced around the central body 54 is a plurality of flat, rigid, plastic strips 86. One end of each of the flat strips 86 must be manually inserted and cemented into the respective slots 88 in the tail 56 of the probe 50. The other end of each flat strip 86 has a stop 87 attached to each outer surface, but is otherwise free to move in grooves 90.

An eddy current coil 94, is manually formed and cemented on the inner surface of each of the flat strips 86. In addition, foam rubber pads 96 must be cemented to the inner side of each flat strip 86 above and below each eddy current coil 94. The pads 96 are necessary to prevent the rubber tube 78 from expanding out between the flat strips 86 and rubbing against the wall of the tube 38 and puncturing.

Electrical leads 97 extend from the eddy current coils 94, along the strips 86, through radial slots (not shown) in the tail 56, through the brushes 72, through the bellows tubing 64 and through the nylon tubing 66 to the external instrumentation.

Because the electrical leads 97 are about the size of a human hair and have to be glued by hand to the strips 86, they are very susceptible to breakage during manual assembly of the probe 50. This is especially true in light of the fact that the overall length of an entire probe 50 is about 3-4 inches.

In order to inflate probe 50, a gas, such as air, is introduced through the vinyl tube 84, through the channel 82 and into the rubber tube 78, thus causing the rubber tube 78 to expand outwardly as shown in FIG. 2. After the rubber tube 78 is inflated, the vinyl tube 84 must be heat sealed, and the hypodermic syringe removed to prevent air leakage from the vinyl tube 84. The inflation of the rubber tube 78 is a "one-time" event, and thus, inflation is preserved throughout operation.

A major drawback of the conventional, inflatable, array coil probe 50 is that the rubber tube 78 is susceptible to puncturing, which causes leakage of air during inflation. The punctures are usually unintentionally made while assembling the various parts of the probe 50.

The probe 50, only after it has been properly inflated, is then inserted into and positioned in the tube 38. When the inflated probe 50 encounters a constriction or other irregularity in the wall of the tube 38, the inflation mechanism 76 is intended to conform to the shape of the inside surface of the tube 38. The external instrumentation records the readings of each eddy current coil 94 during operation in an attempt to detect defects in the inner wall of a tube 38.

Although the conventional, inflatable array coil probe described above and shown in FIG. 2 overcomes some of the problems inherent in inspecting tubing, inflatable, array coil probes are characterized by the following additional drawbacks:

1. High coil face wear due to the fact that the probe remains inflated during positioning and movement in the tubes;
2. High strain for the electrical leads since these fine wires and their connections to the coils are effectively loose and exposed;
3. Very complex mechanical hardware and electrical wiring leading to expensive and relatively slow assembly; and
4. Essentially limited to use on straight sections due to minimal flexibility.

Therefore, a need still exists for a probe that is capable of remotely inspecting tubes with great accuracy and efficiency.

SUMMARY OF THE INVENTION

Accordingly, it is an object of the present invention to provide an inspection device which can more accurately and reliably detect defects in tubes.

It is another object of the present invention to provide an inflatable, eddy current inspection probe having lower coil face wear and lower susceptibility to puncture than conventional, inflatable probes.

It is another object of the present invention to provide an inflatable, eddy current inspection probe having built-in strain relief for the electrical leads and having less incidence of lead breakage during manufacture.

It is another object of the present invention to provide an inflatable, eddy current inspection probe flexible enough to permit the inspection of relatively small U-bends.

It is another object of the present invention to provide a method for assembling an inspection device more quickly and at a lower cost than the methods of the prior art.

Finally, it is an object of the present invention to provide a method for assembling an inflatable, eddy current inspection probe, wherein the coils and electrical leads are enclosed in a molded, inflatable body, thus effecting easier and less costly manufacture.

To achieve the foregoing and other objects of the present invention, and in accordance with the purpose of the invention, there is provided an eddy current inspection probe having an injection molded, inflatable, central body including radially disposed eddy current coils and electrical leads embedded in the central body. The central body can be inflated at will by injection of a fluid through a pressure hose connected thereto to produce intimate contact between the coils and the inside wall of a tube.

The present invention is also directed to a method for assembling the eddy current inspection probe described above, comprising the steps of: uniformly spacing a plurality of eddy current coils within a mold capable of producing an inflatable central body which is cylindrical, hollow and externally ribbed and which has a nose and a tail molded integrally thereof; arranging electrical leads in the mold so that they will extend from each eddy current coil and through the inflatable, central body; introducing a plastic material, such as urethane, into the mold; passing the leads through the tail, around a pressure hose attached to the tail and onto the external instrumentation; and attaching first and second positioning mechanisms to the nose and tail, respectively, to complete the probe.

The probe of the present invention exhibits lower, coil-face wear than the conventional, inflatable, array coil probe described above due to the fact that the probe of the present invention can be expanded after being positioned in the tube and does not have to be expanded before. In addition, the probe of the present invention has built-in strain relief for the electrical coil leads since they are enclosed in the molded central body, and the leads are less prone to breakage during assembly. Further, compared to the very complex mechanical hardware and electrical wiring of conventional probes, the molded nature of the present invention permits easier, less expensive manufacturing. In addition, the molded, central body is less susceptible to puncturing and is more adaptive to differing sizes of tubes than the prior art probes. Finally, the inflatable, central body of the present invention is flexible enough to permit easier and more accurate inspection of relatively smaller, non-straight areas of the tubes than conventional probes.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE PREFERRED EMBODIMENTS

Figure 3:
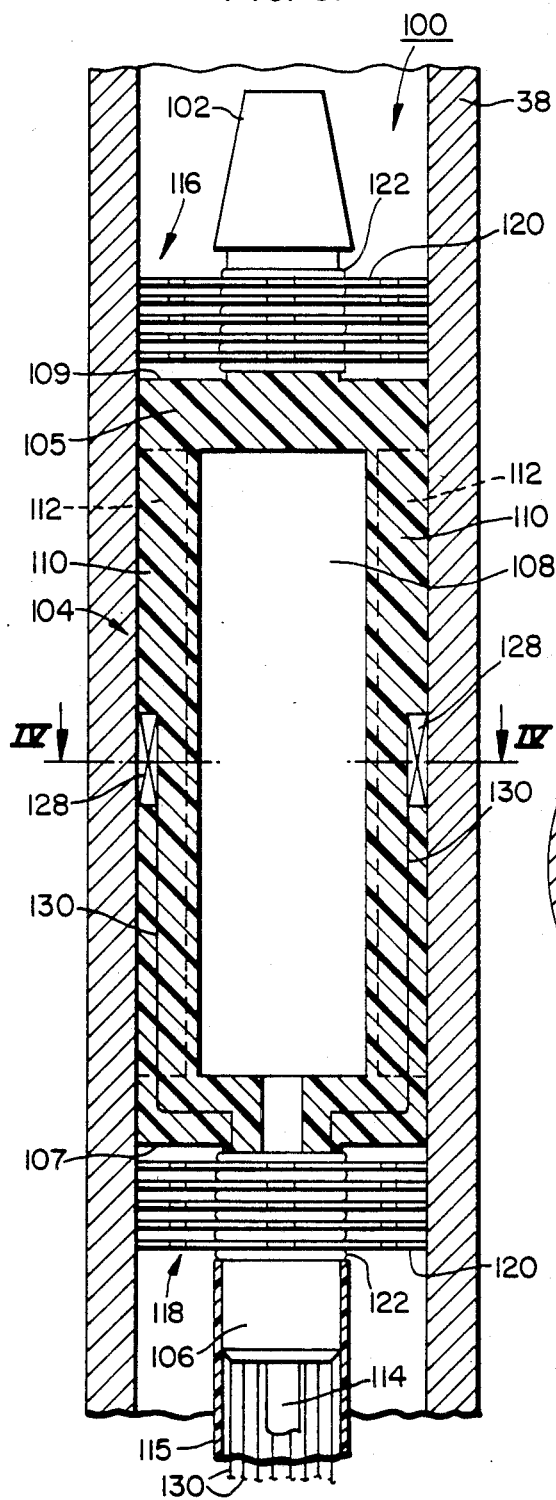
FIG. 3 is an elevational, partial cross-sectional view of the inflatable eddy current inspection probe of the present invention positioned in a tube, illustrating particularly the enclosed nature of the coils and leads within the molded body.
Figure 4:
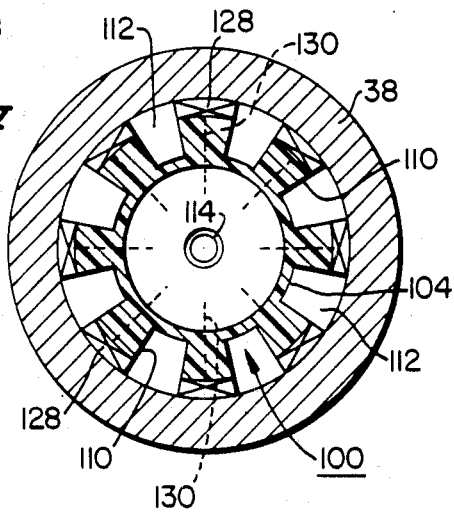
FIG. 4 is a cross-sectional view of the probe of the present invention taken along lines IV—IV of FIG. 3.

In contrast to the conventional inspection probe 50 described above, the "balloon" inspection probe of the present invention for inspecting tubes 38 is shown in FIGS. 3 and 4 and is referred to by reference numeral 100.

More particularly, FIG. 3 is an elevational, cross-sectional view of the inspection probe 100 of the present invention within a tube 38. The probe 100 comprises, most importantly, a central body 104. The central body 104 includes a cylindrical member 105 which is preferably injection molded of a plastic, such as urethane, or cast of rubber. Hereafter, the term "molded" will be used to synonymously represent injection molding, casting or other similar procedures, all of which are contemplated by the present invention.

The cylindrical member 105 has a first end 107, a second end 109, a hollow core 108 and a plurality of ribs 110 formed at the outer surface of the cylindrical member 105. Each rib 110 is flanked by indentations 112 formed in the outer surface of the cylindrical member 105.

Although the preferred embodiment shown in FIGS. 3 and 4 includes a plurality of parallel, straight ribs 110 extending along the sides of the cylindrical member 105, the ribs 110 can be formed so that one or more spiral ribs are formed around the cylindrical member 105. Spiral ribs 110 can provide less expansion of the ribs during inflation of the probe 100, if so desired.

As shown in FIGS. 3 and 4, the central body 104 also comprises a uniformly spaced plurality of eddy current coils 128. Each coil 128 is located at about the midpoint of each rib 110 in close proximity to the surface thereof. The number of coils 128 to be located around the circumference of the probe 100 is variable, although eight is preferred. Full 360° coverage of the tube wall can be achieved by a dual body probe with overlapping coils.

Electrical leads 130 extend from each eddy current coil 128, through each rib 110 of the cylindrical member 105 and out of the first end 107 of the cylindrical member 105. With the present invention, built-in strain relief is provided for the electrical leads 130 since these fine wires are actually embedded in the molded central body 104 of the probe 100.

As seen in FIG. 3, the nose 102 and the tail 106 of the present invention are substantially similar in outward appearance to the conventional nose 52 and tail 56 described above. However, the nose 102 and the tail 106 are preferably integrally molded of the cylindrical member 105. Alternatively, the nose 102 and/or the tail 106 can be formed separately from the cylindrical member 105 and attached thereto.

A long pressure hose 114 made of, e.g., nylon tubing is attached to the tail 106 and is in communication with the hollow core 108. The pressure hose 114 is responsible for inflating the central body 104, as will be described.

As can be seen in FIG. 3, the leads 130 extending through the tail 106, are located around the pressure hose 114 and extend to the external instrumentation.

Further, a relatively rigid, nylon tube 115 is attached to the tail 106 for pushing the probe 100 through the tube 38. In addition, a first positioning mechanism 116 is mounted on the nose 102, while a second positioning mechanism 118 is mounted on the tail 106, so as to provide means by which the probe 100 can be centrally oriented within a particular tube 38. The first positioning mechanism 116 and the second positioning mechanism 118 may comprise brushes 120 attached by rubber O-rings 122, as is conventional. Finally, an emergency cable (not shown) can be attached to the probe 100, if desired.

The above-described structure of the preferred embodiment of the probe 100 and, in particular, the plurality of ribs 110 formed therein, provides uniform inflation of the probe 100 and superior flexibility.

During operation, the probe 100 is first inserted into the area to be inspected and then inflated to collect the appropriate data. As suggested above, the pressure hose 114 supplies water or air pressure from an external pump (not shown) to the hollow 108 of the central body 104. This causes the central body 104 to expand outwardly, thus producing contact between the surface riding coils 128 in the internal surface of the tubes 38, as shown in FIGS. 3 and 4.

The pressure tube 114 can also withdraw air or fluid from the hollow 108, when desired, to deflate the central body 104 for easier movement of the probe 100 through the tube 38.

In addition, if a small puncture exists in the central body 104, the inflated state can be maintained by increasing the fluid pressure injected into the central body 104 via the pressure hose 114. In contrast, the conventional, inflatable array coil probe is inoperable if a puncture exists; it has to be disassembled and repaired.

FIG. 4 also illustrates the method for assembling the probe 100. The method comprises uniformly spacing the plurality of eddy current coils 128 within a mold (not shown). A person having ordinary skill in the plastic material molding art would be capable of preparing such a mold. The mold should be capable of producing a cylindrical member 105 having a first end 107 including a tail 106, the hollow portion 108, a second end 109 including a nose 102 and a plurality of ribs 110 flanked by indentations 112. Each coil 128 is placed at about the midpoint of each intended rib 110.

Electrical leads 130 are then arranged in the mold so that they will extend from each eddy current coil 128 through the cylindrical member 105 and out of the first end 107 of the cylindrical member 105. A plastic material, such as urethane or rubber is then introduced into the mold, which covers the coils 128 and the lead 130 attached to each coil 128.

After the central body 104 is molded, the first and second positioning mechanisms 116 and 118 can be attached. The protruding ends of the leads 130 are then positioned around the pressure hose 114 attached to the tail 106 of the cylindrical member 105 and through to the external instrumentation. Finally, the nylon tube 115 is slipped over the pressure hose 114 and the leads 130.

Accordingly, the present invention results in lower coil 128 face wear than the conventional probe 50 due to the fact that the present probe 100 is only inflated when in place and not during insertion into, through and out of the tube 38. Of course, this procedure is in direct contrast to the operation of the conventional probe 50 which must be inflated and sealed prior to positioning.

In addition, since the conventional probe 50 must be inflated before positioning within the tube 38, it often encounters resistance as it is being pushed into the tube 38 for positioning. In contrast, the uninflated probe 100 of the present invention can be inserted into a tube 38 and pushed to the far end of the tube 38 with little or no interference. Then, the probe 100 can be inflated and pulled back through the tube 38 to inspect the entire tube 38.

Further, the probe 100 of the present invention, and particularly the inflatable central body 104, is flexible enough to permit the inspection of relatively small U-bends without any special modifications in overall inspection probe design. The conventional probe 50 described above is not as adaptive because of the relatively rigid central body 54 required thereby.

Figure 1:
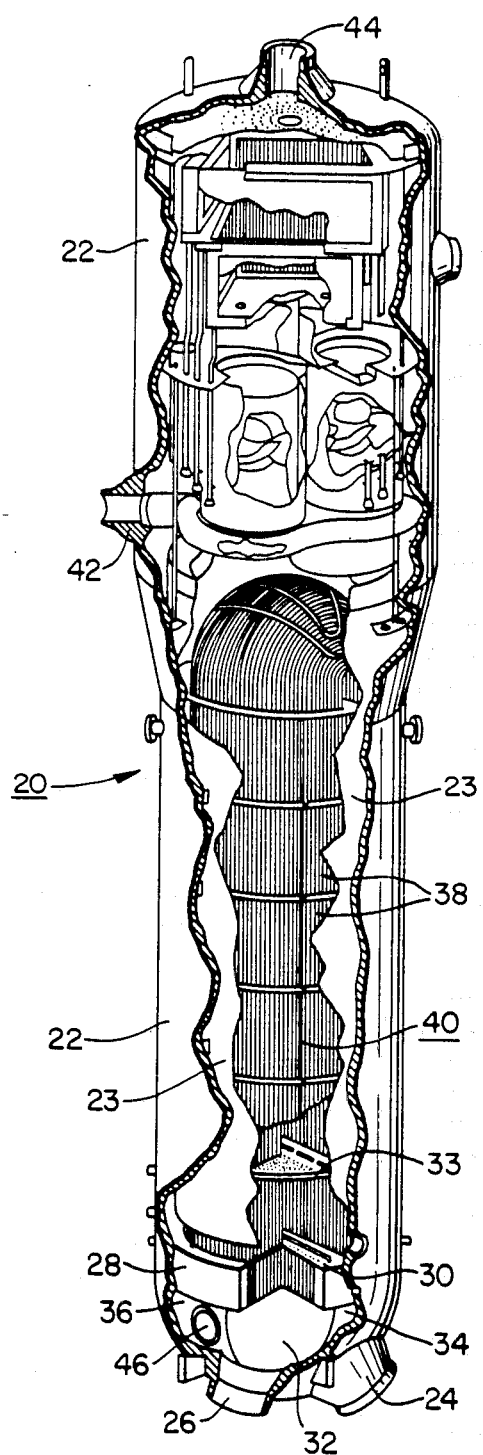
FIG. 1 is an elevational, cut-away view of a conventional nuclear steam generator, illustrating particularly the tube bundle in the lower section thereof.
Figure 2:
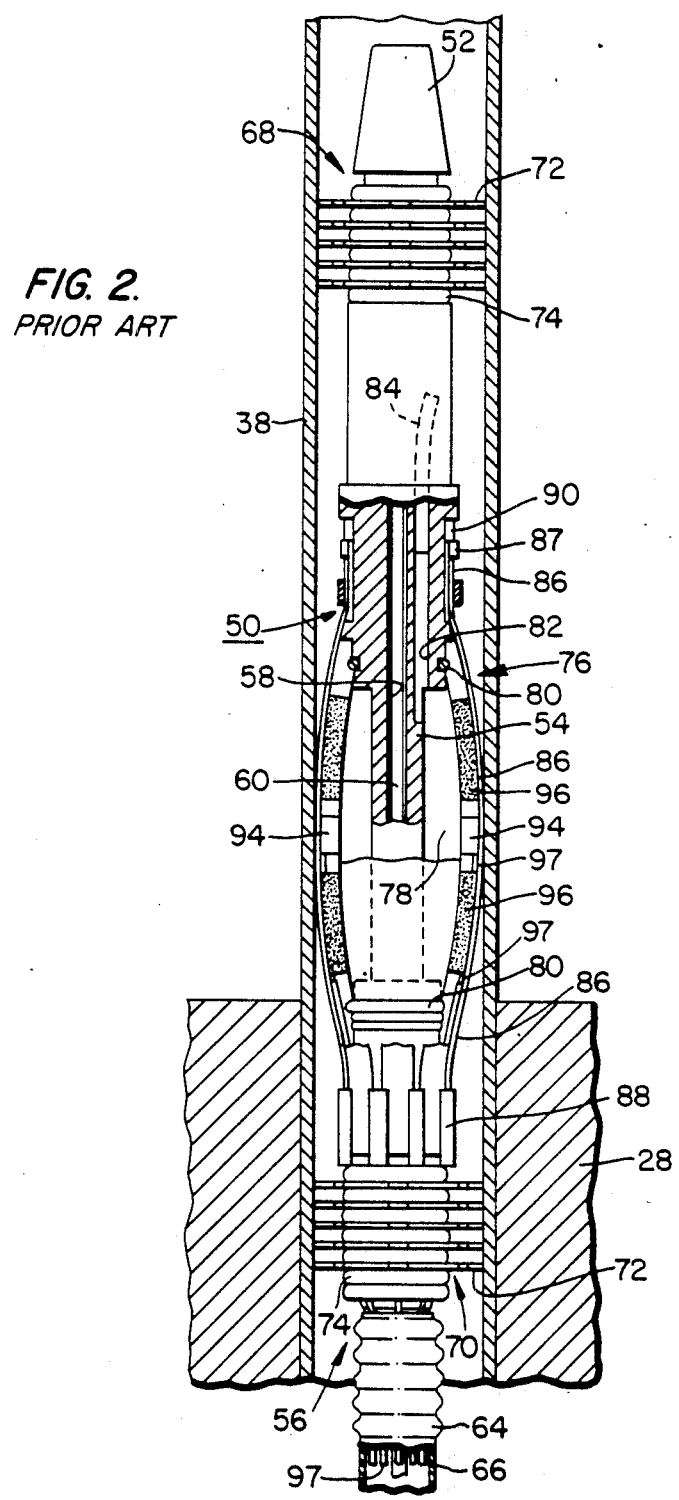
FIG. 2 is an elevational, partial cross-sectional view of a conventional, inflatable array coil probe positioned in a tube, illustrating particularly the plurality of external strips for abutting the internal surfaces of the tube.

Greater sensitivity is also provided by the probe of the present invention relative to the conventional, inflatable probe 50 because the thickness of the plastic material between the coils 128 and the wall of the tube 38 can be less than the thickness of the flat strips 86 of the conventional probe 50 shown in FIG. 2. Further, the probe 100 of the present invention, due to the predictable inflatable nature of the central body 104, is capable of adaptation to a greater diameter of tubes 38 than any of the conventional probes discussed above.

The probe 100 of the present invention also does not require that pads be cemented to the inner sides of flat strips above and below each eddy current coil, as is true of the conventional probe 50 discussed above. In addition, the coils 128 and leads 130 of the present invention do not have to be manually attached to the probe 100; these coils 128 and leads 130 are merely placed in the mold before the central body 104 is molded. Accordingly, in contrast to the conventional, inflatable, array coil probe 50 discussed above, which involves very complex mechanical hardware and electrical wiring, the probe 100 of the present invention is easier and less expensive to construct. Overall, manufacturing of probes is simplified with the present invention and made more cost efficient.

The foregoing is considered as illustrative only of the principles of the invention. Further, since numerous modifications and changes will readily occur to those skilled in the art, it is not desired to limit the invention to the exact construction and operation shown and described and, accordingly, all suitable modifications and equivalents may be resorted to, falling within the scope of the invention and the appended claim and its equivalents. For example, it is to be understood that the probe of the present invention can be used with any tubing that requires inspection, such as tubing in non-nuclear heat exchangers.

I claim:
1. An inspection device for internally inspecting a tube, comprising:
    (a) a molded, inflatable, hollow, flexible, central body, including
        (i) a wall having a plurality of elongated ribs formed integrally thereof, each having an external surface,
        (ii) a first end including a tail with a positioning means connected thereto which is capable of extending into contact with the tube for positioning the device within the tube,
        (iii) a second end including a nose with a positioning means connected thereto which is capable of extending into contact with the tube for positioning the device within the tube,
        (iv) a coil disposed approximately midway longitudinally within each of the plurality of elongated ribs adjacent to the external surface thereof, and
        (v) a lead extending from each coil, within the wall of the central body and out the first end of the central body; and
    (b) flexible means having an end connected to the first end of the central body for inflating the central body, introducing and withdrawing the device relative to the tube, and receiving the leads extending from the first end of the central body,
    wherein, when the central body is introduced into the tube and inflated, each of the coils is placed in close proximity with the tube.

* * * * *